US 9,999,398 B2

(12) United States Patent
Rees et al.

(10) Patent No.: US 9,999,398 B2
(45) Date of Patent: Jun. 19, 2018

(54) PRESENTING DATA GENERATED BY A CONTINUOUS GLUCOSE MONITOR

(71) Applicant: Roche Diagnostics Operations, Inc., Indianapolis, IN (US)

(72) Inventors: Christen A. Rees, Indianapolis, IN (US); Sheldon A. White, Westfield, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 973 days.

(21) Appl. No.: 14/017,776

(22) Filed: Sep. 4, 2013

(65) Prior Publication Data

US 2015/0061890 A1    Mar. 5, 2015

(51) Int. Cl.
| | |
|---|---|
| *A61B 5/00* | (2006.01) |
| *A61M 5/172* | (2006.01) |
| *A61B 5/145* | (2006.01) |
| *H04L 12/815* | (2013.01) |
| *G06F 19/00* | (2018.01) |
| *H04L 29/08* | (2006.01) |

(52) U.S. Cl.
CPC ............ *A61B 5/74* (2013.01); *A61B 5/14532* (2013.01); *A61M 5/1723* (2013.01); *G06F 19/3456* (2013.01); *H04L 47/22* (2013.01); *G06F 19/3468* (2013.01); *H04L 67/12* (2013.01); *H04L 67/322* (2013.01)

(58) Field of Classification Search
CPC .............. A61B 5/14532; A61B 5/0002; A61B 2560/0271; A61B 5/00; A61B 5/4839; G06F 19/3418; G06F 19/324; G06F 19/326; G06F 9/546; H04L 67/12; H04L 12/1895

USPC .................. 340/870.01–870.44, 500–693.12, 340/5.1–5.92; 455/67.11
See application file for complete search history.

(56) References Cited

U.S. PATENT DOCUMENTS

| | | | |
|---|---|---|---|
| 6,425,060 B1 | 7/2002 | Mounes-Toussi et al. | |
| 7,811,231 B2 | 10/2010 | Jin et al. | |
| 8,187,183 B2 | 5/2012 | Jin et al. | |

(Continued)

FOREIGN PATENT DOCUMENTS

| | | |
|---|---|---|
| CN | 103168304 A | 6/2013 |
| CN | 103238154 A | 8/2013 |
| RU | 2473307 C1 | 1/2013 |

*Primary Examiner* — Firmin Backer
*Assistant Examiner* — Jerold Murphy
(74) *Attorney, Agent, or Firm* — Harness Dickey (57) ABSTRACT

A computer implemented method for transmitting messages generated by a continuous glucose monitor (CGM), the method comprising: generating a first message at the CGM at a first time, the first message being related to blood glucose measuring; generating a second message at the CGM at a second time, the second time being after the first time, the second message being related to blood glucose measuring; determining an elapsed time since a transmitter of the CGM has transmitted data; determining whether the elapsed time is greater than a threshold; determining whether the second message is to be transmitted before the first message, in response to the elapsed time being greater than the threshold; and transmitting data corresponding with the second message before transmitting data corresponding with the first message to a diabetes management device, in response to determining that the second message is to be transmitted before the first message.

14 Claims, 8 Drawing Sheets

(56) References Cited

U.S. PATENT DOCUMENTS

| | | |
|---|---|---|
| 2004/0186365 A1 | 9/2004 | Jin et al. |
| 2005/0078672 A1* | 4/2005 | Caliskan ................ H04L 45/42 370/389 |
| 2006/0168013 A1* | 7/2006 | Wilson ............... G05B 19/4184 709/206 |
| 2007/0253021 A1* | 11/2007 | Mehta .................. A61B 5/0002 358/1.15 |
| 2008/0092638 A1 | 4/2008 | Brenneman et al. |
| 2010/0010330 A1 | 1/2010 | Rankers et al. |
| 2011/0028817 A1 | 2/2011 | Jin et al. |
| 2011/0099338 A1 | 4/2011 | Binz et al. |
| 2011/0193699 A1* | 8/2011 | Van Acht ........... A63B 24/0006 340/540 |
| 2011/0193704 A1 | 8/2011 | Harper et al. |
| 2012/0176895 A1 | 7/2012 | Jiang et al. |
| 2014/0266785 A1* | 9/2014 | Miller ................ H04W 76/023 340/870.04 |

* cited by examiner

PRESENTING DATA GENERATED BY A CONTINUOUS GLUCOSE MONITOR

FIELD

The present disclosure relates generally to medical devices and more particularly to a system and method for presenting data generated by a continuous glucose monitor.

BACKGROUND

Advances in medical technology have resulted in medical devices that allow patients to manage their medical conditions with relative ease. For example, several decades ago, a patient suffering from diabetes would have found it difficult to monitor and control the level of glucose in his bloodstream on his own. Today, however, a patient suffering from diabetes can monitor the level of glucose in his bloodstream using a portable blood glucose monitor and, if needed, administer a dosage of insulin to control the level of glucose in his bloodstream.

Some blood glucose monitors, such as a continuous glucose monitor (CGM), continuously generate raw data which corresponds to the level of glucose in a patient's bloodstream. Some CGMs transmit the generated data to a diabetes management device. Other devices, such as an insulin infusion pump, can also generate data and transmit the data to the diabetes management device. The sheer amount of data generated by the CGM and received by the diabetes management device can overwhelm a patient who is using the diabetes management device. Thus, there is a need to present the data in a more manageable manner.

This section provides background information related to the present disclosure which is not necessarily prior art.

SUMMARY

The present application discloses a computer implemented method for transmitting messages that are generated by a continuous glucose monitor (CGM). The method includes: generating a first message at the CGM at a first time, the first message being related to blood glucose measuring; generating a second message at the CGM at a second time, the second message being related to blood glucose measuring, where the second time is after the first time; determining, by a processor, an elapsed time since a transmitter of the CGM has transmitted data; determining, by the processor, whether the elapsed time is greater than a first threshold; determining, by the processor, whether the second message is to be transmitted before the first message, in response to the elapsed time being greater than the first threshold; and transmitting, via the transmitter, data corresponding with the second message before transmitting data corresponding with the first message to a diabetes management device, in response to determining that the second message is to be transmitted before the first message.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

Figure 1:
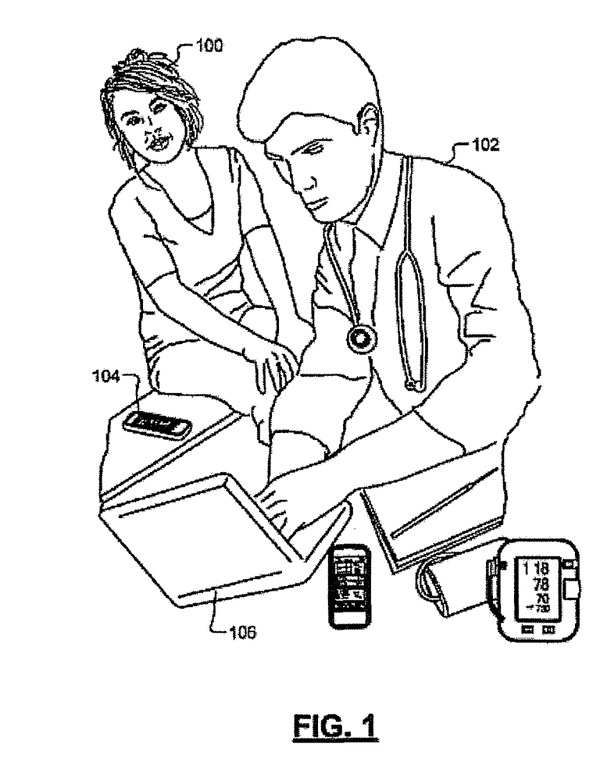
FIG. 1 is a diagram illustrating a patient and a treating clinician.

Referring now to FIG. 1, a person 100 with diabetes and a healthcare professional 102 are shown in a clinical environment. Persons with diabetes include persons with metabolic syndrome, pre-diabetes, type 1 diabetics, type 2 diabetics and gestational diabetics and are collectively referred to as a patient. Healthcare providers for diabetes are diverse and include nurses, nurse practitioners, physicians, and endocrinologists and are collectively referred to as a clinician. While reference is made to diabetes, this description extends to other chronic diseases.

During a healthcare consultation, the patient 100 typically shares with the clinician 102 a variety of patient data including blood glucose measurements, continuous glucose monitor data, amounts of insulin infused, amounts of food and beverages consumed, exercise schedules, and other lifestyle information. The clinician 102 can obtain additional patient data that includes measurements of HbA1C, cholesterol levels, triglycerides, blood pressure, and weight of the patient 100. The patient data can be recorded manually or electronically on a handheld diabetes managing device 104, a diabetes analysis software executed on a personal computer (PC) 106, and/or a web-based diabetes analysis site (not shown). The clinician 102 can analyze the patient data manually or electronically using the diabetes analysis software and/or the web-based diabetes analysis site. After analyzing the patient data and reviewing adherence of the patient 100 to previously prescribed therapy, the clinician 102 can decide whether to modify the therapy for the patient 100.

Figure 2:
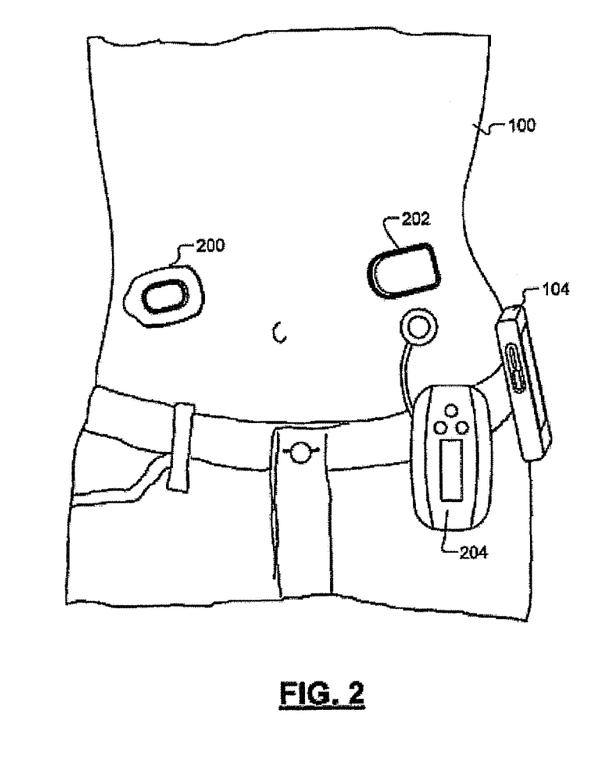
FIG. 2 is a diagram illustrating a patient with a continuous glucose monitor (CGM), an ambulatory durable insulin infusion pump, an ambulatory non-durable insulin infusion pump, and a diabetes management device (diabetes manager)

Referring now to FIG. 2, the patient 100 can use a continuous glucose monitor (CGM) 200, an ambulatory durable insulin infusion pump 202 or an ambulatory non-durable insulin infusion pump 204 (collectively insulin pump 202 or 204), and the handheld diabetes managing device 104 (hereinafter the diabetes manager 104). The CGM 200 uses a subcutaneous sensor to sense and monitor the amount of glucose in the blood of the patient 100 and communicates corresponding readings to the handheld diabetes managing device 104.

The diabetes manager 104 performs various tasks including measuring and recording blood glucose levels, determining an amount of insulin to be administered to the patient 100 via the insulin pump 202 or 204, receiving patient data via a user interface, archiving the patient data, etc. The diabetes manager 104 periodically receives readings from the CGM 200 indicating glucose level in the blood of the patient 100. The diabetes manager 104 transmits instructions to the insulin pump 202 or 204, which delivers insulin to the patient 100. Insulin can be delivered in the form of a bolus dose, which raises the amount of insulin in the blood of the patient 100 by a predetermined amount. Additionally, insulin can be delivered in a scheduled manner in the form of a basal dose, which maintains a predetermined insulin level in the blood of the patient 100.

Figure 3:
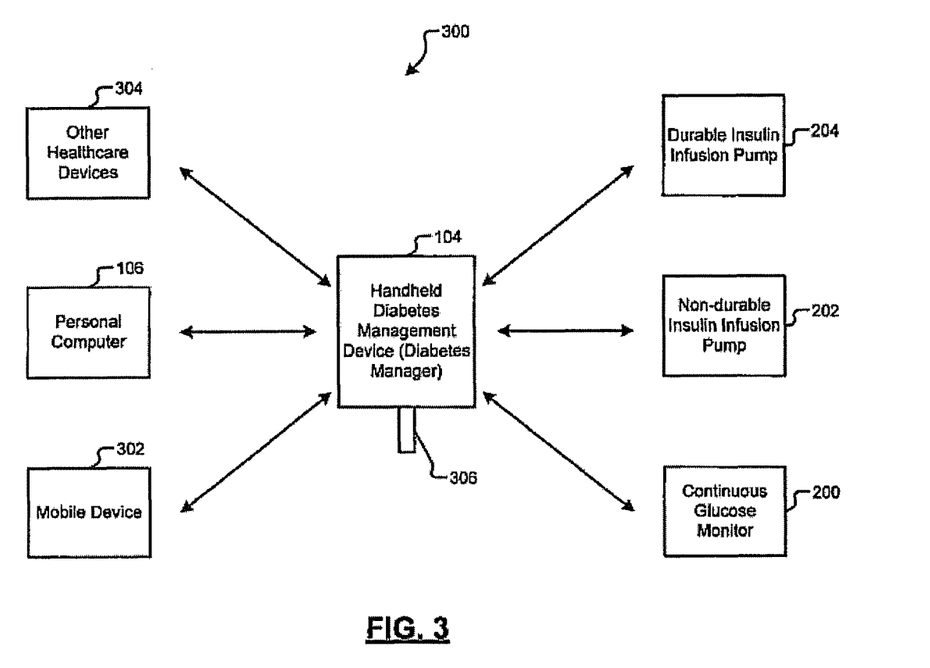
FIG. 3 is a block diagram illustrating an example diabetes care system used by patients and clinicians to manage diabetes.

Referring now to FIG. 3, a diabetes management system 300 used by the patient 100 and the clinician 102 includes one or more of the following devices: the diabetes manager 104, the continuous glucose monitor (CGM) 200, the insulin pump 202 or 204, a mobile device 302, the diabetes analysis software on the PC 106, and other healthcare devices 304. The diabetes manager 104 is configured as a system hub and communicates with the devices of the diabetes management system 300. Alternatively, the insulin pump 204 or the mobile device 302 can serve as the system hub. Communication between the various devices in the diabetes management system 300 can be performed using wireless interfaces (e.g., Bluetooth, Wireless Local Area Network (WLAN), Near Field Communications (NFC), ZigBee, etc) and/or wireline interfaces (e.g., USB, Ethernet, etc). Communication protocols used by these devices can include protocols compliant with the IEEE 11073 standard as extended using guidelines provided by Continua® Health Alliance Design Guidelines. Further, healthcare records systems such as Microsoft® HealthVault™ can be used by the patient 100 and clinician 102 to exchange information.

The diabetes manager 104 can receive glucose readings from one or more sources (e.g., from the CGM 200). The CGM 200 continuously measures the glucose level of the patient 100. The CGM 200 periodically communicates the glucose level to the diabetes manager 104.

Additionally, in an example embodiment, the diabetes manager 104 includes a blood glucose measuring (BGM) sensor and a port that communicates with the BGM sensor (both not shown). The port can receive a blood glucose measurement strip 306. The patient 100 deposits a sample of blood or other bodily fluid on the blood glucose measurement strip 306. The BGM sensor analyzes the sample and measures the blood glucose level in the sample. The blood glucose level measured from the sample and/or the glucose level read by the CGM 200 can be used to determine the amount of insulin to be administered to the patient 100.

The diabetes manager 104 communicates with the insulin pump 202 or 204. The insulin pump 202 or 204 can be configured to receive instructions from the diabetes manager 104 to deliver a predetermined amount of insulin to the patient 100. Additionally, the insulin pump 202 or 204 can receive other information including meal and/or exercise schedules of the patient 100. The insulin pump 202 or 204 can determine the amount of insulin to administer based on the additional information.

The insulin pump 202 or 204 can also communicate data to the diabetes manager 104. The data can include amounts of insulin delivered to the patient 100, corresponding times of delivery, and pump status. The diabetes manager 104 and the insulin pump 202 or 204 can communicate using a wireless communication protocol such as Bluetooth. Other wireless or wireline communication protocols can also be used.

In addition, the diabetes manager 104 can communicate with other healthcare devices 304. For example, the other healthcare devices 304 can include a blood pressure meter, a weight scale, a pedometer, a fingertip pulse oximeter, a thermometer, etc. The other healthcare devices 304 obtain and communicate personal health information of the patient 100 to the diabetes manager 104 through wireless, USB, or other interfaces. The other healthcare devices 304 use communication protocols compliant with ISO/IEEE 11073 extended using guidelines from Continual® Health Alliance. The diabetes manager 104 can communicate with the other healthcare devices 304 using interfaces including Bluetooth, USB, etc. Further, the devices of the diabetes management system 300 can communicate with each other via the diabetes manager 104.

The diabetes manager 104 can communicate with the PC 106 using Bluetooth, USB, or other interfaces. A diabetes management software running on the PC 106 includes an analyzer-configurator that stores configuration information of the devices of the diabetes management system 300. The configurator has a database to store configuration information of the diabetes manager 104 and the other devices. The configurator can communicate with users through standard web or computer screens in non-web applications. The configurator transmits user-approved configurations to the devices of the diabetes management system 300. The analyzer retrieves data from the diabetes manager 104, stores the data in a database, and outputs analysis results through standard web pages or computer screens in non-web based applications.

The diabetes manager 104 can communicate with the mobile device 302 using Bluetooth. The mobile device 302 can include a cellular phone, a PDA, or a pager. The diabetes manager 104 can send messages to an external network through the mobile device 302. The mobile device 302 can transmit messages to the external network based on requests received from the diabetes manager 104. In an example embodiment, the diabetes manager 104 includes a mobile electronic communication device, such as a mobile phone or a smartphone.

The CGM 200 uses a subcutaneous sensor to sense and monitor a physical attribute related to the glucose level of the patient 100. In some embodiments, the CGM 200 measures the level of glucose in the interstitial fluid of the patient 100, which is related to the glucose level of the patient 100. The level of glucose in the interstitial fluid of the patient 100 may be sensed by the CGM 200 by sampling an electrical characteristic, such as current. The sampled current, and therefore the level of glucose in the interstitial fluid, is related to the glucose level of the patient 100. In order to accurately estimate the glucose level of the patient 100 based on the physical attribute (current, etc.) measured by the CGM 200, the diabetes manager 104 can be periodically calibrated. While the remainder of this description is related to associating a current sensed by the CGM 200 to an estimated glucose level of the patient 100, one skilled in the art will appreciate that any physical attribute related to the glucose level of the patient 100 may be utilized instead.

The diabetes manager 104 can be calibrated by determining calibration data based on at least one current sample and at least one blood glucose measurement. The calibration data can take many forms, but is essentially data sufficient to convert the current sampled by the CGM 200 to an estimated glucose level of the patient 100. The current sampled by the CGM 200 and the glucose level of the patient 100 can be assumed to have a linear relationship within a normal measurement region of approximately 40 to 400 Milligrams per Deciliter. Based on this assumed linear relationship, the calibration data can be sufficient to identify a linear equation that associates one or more current samples with an estimated glucose level of the patient. For example, the calibration data can be one or more coefficients of a linear equation. After calibration, the diabetes manager 104 can determine an estimated glucose level of the patient 100 based on the calibration data and the current sampled by the CGM 200.

Figure 4:
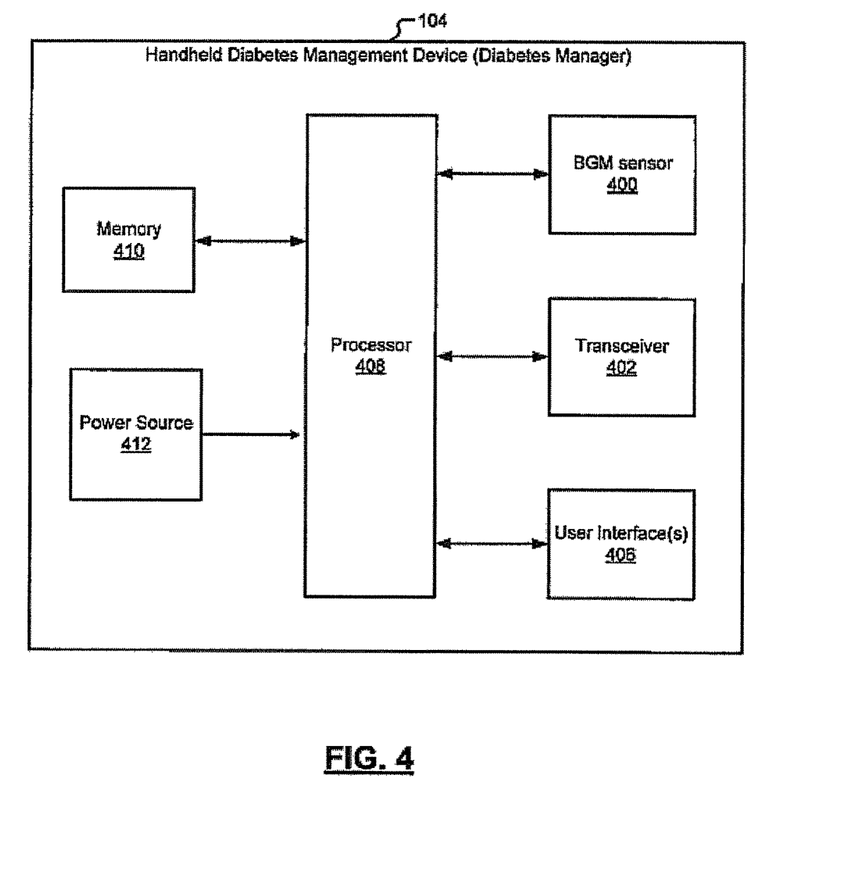
FIG. 4 is a block diagram illustrating an example diabetes manager.

Referring now to FIG. 4, an exemplary diabetes manager 104 includes a blood glucose measuring (BGM) sensor 400, a transceiver 402, user interfaces 406, a processor 408, memory 410, and a power source 412. The BGM sensor 400 includes a blood glucose measuring engine that analyzes samples provided by the patient 100 on the blood glucose measurement strip 306 and that measures the amount of blood glucose in the samples. The transceiver 402 can include multiple radios that communicate with different devices of the diabetes management system 300. The transceiver 402 includes a Bluetooth transceiver that can operate in a Bluetooth low energy mode. In other embodiments, the transceiver 402 includes one or more of a Wireless Local Area Network (WLAN) transceiver, a Near Field Communications (NFC) transceiver, a ZigBee transceiver, a cellular transceiver and an infrared (IR) transceiver. The user interfaces 406 include an output interface and an input interface. The user interfaces 406 can include keys, switches, a display, a touchscreen display, a speaker, a microphone, a vibration motor for haptics, a secure digital (SD) card port, and/or a USB port (all not shown).

The processor 408 processes data received from the BGM sensor 400, the transceiver 402, and the user interfaces 406. The processor 408 uses memory 410 for processing and storing data. The memory 410 can include volatile and nonvolatile memory. The processor 408 outputs data to and receives data from the user interfaces 406. The processor 408 outputs data to and receives data from the devices of the diabetes management system 300 via the transceiver 402. The power source 412 supplies power to the components of the diabetes manager 104. The power source 412 can include a rechargeable battery or other source of power. The battery can be recharged, e.g., by using an adapter that plugs into a wall outlet and/or via a USB port on the diabetes manager 104.

Figure 5:
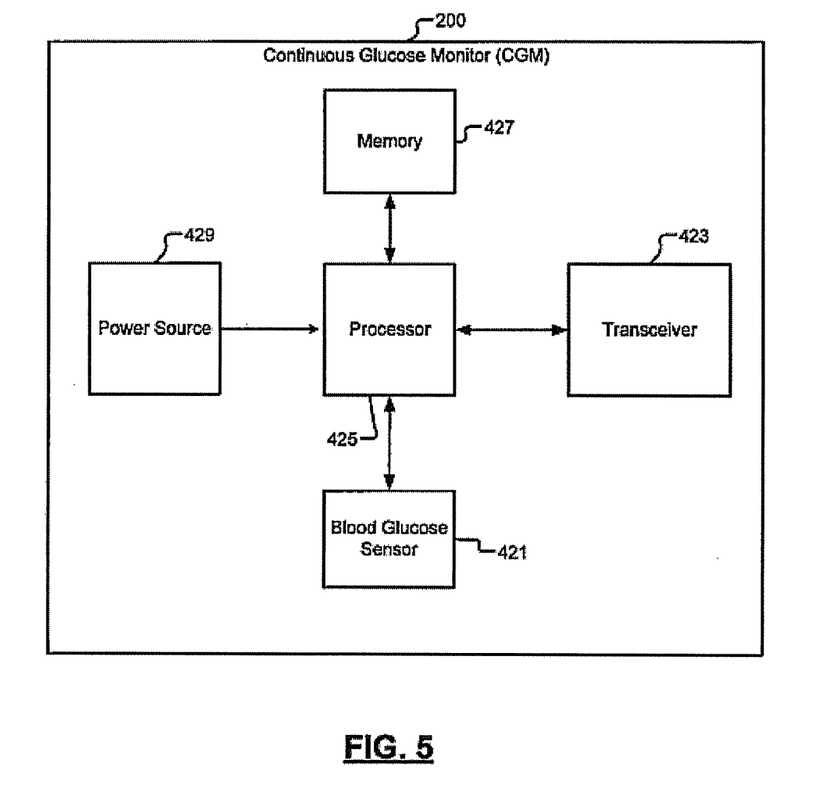
FIG. 5 is a block diagram illustrating an example CGM.

Referring now to FIG. 5, an exemplary continuous glucose monitor (CGM) 200 includes a blood glucose sensor 421, a transceiver 423, a processor 425, memory 427, and a power source 429. The sensor 421 can monitor a condition of the patient 100 that is related to the glucose level of the patient 100. For example, the sensor 421, alone or in combination with processor 425, can periodically sample a current value that corresponds to the level of glucose in the interstitial fluid of the patient 100. The transceiver 423 can include one or more radios that communicate with different devices of the diabetes management system 300. In this embodiment, the transceiver 423 includes a Bluetooth transmitter that transmits data to the transceiver 402 of the diabetes manager 104.

The processor 425 processes data received from the sensor 421 and the transceiver 423. The processor 425 uses memory 427 for processing and storing data. The memory 427 can include volatile and nonvolatile memory. The memory 427 can be utilized to store information related to the configuration of the CGM 200, for example, definitions of measuring duration, failsafe limits and mathematical definitions and settings. The processor 425 outputs data to and receives data from the devices of the diabetes management system 300 via the transceiver 423. The power source 429 supplies power to the components of the CGM 200. The source of power may include a battery that can be recharged, e.g., by using an adapter that plugs into a wall outlet.

Figure 6:
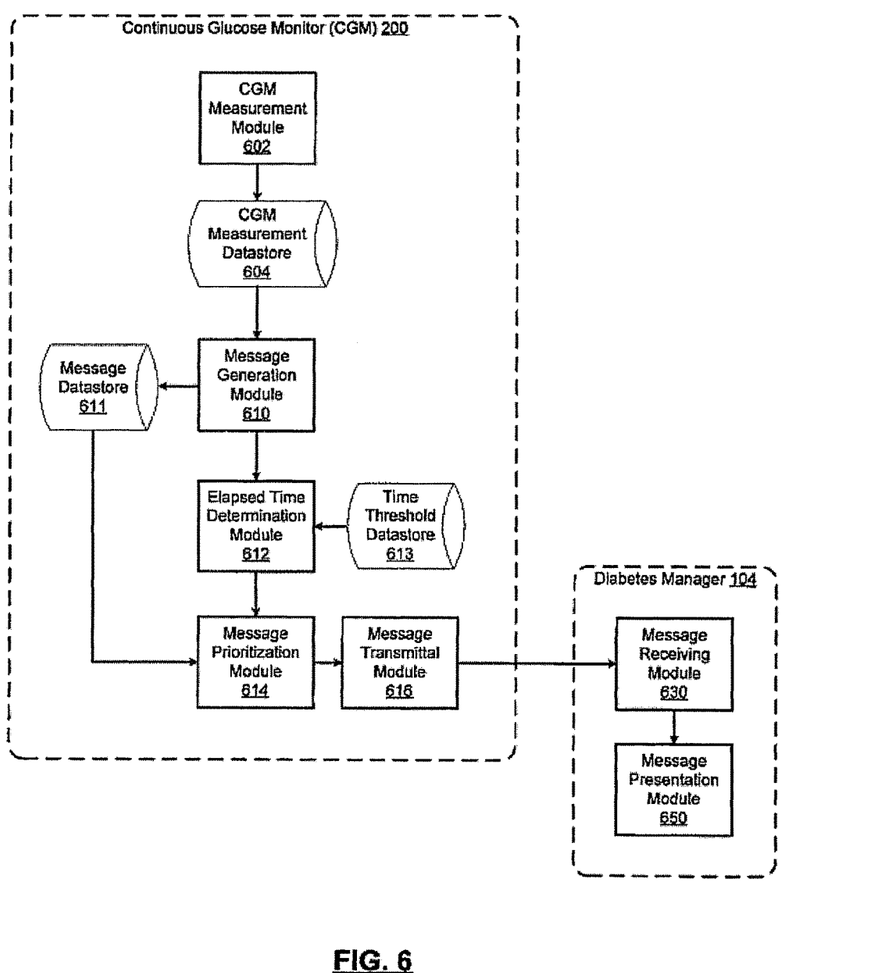
FIG. 6 is a block diagram illustrating an example CGM and an example diabetes manager.

FIG. 6 is a block diagram illustrating an example embodiment in which the CGM 200 is interfaced with the diabetes manager 104. The CGM 200 includes a CGM measurement module 602, a CGM measurement datastore 604, a message generation module 610, an elapsed time determination module 612, a message prioritization module 614 and a message transmittal module 616.

The CGM measurement module 602 acquires blood glucose measurements using the blood glucose sensor 421. The CGM measurement module 602 stores the blood glucose measurements in the CGM measurement datastore 604. Each CGM measurement is stored in a variable length structure that contains a size field, a glucose concentration field, a time offset and a sensor status annunciation field. The CGM measurement has a length ranging from 5 octets to 8 octets, as shown below:

| | LSO ... MSO Size | CGM Glucose Concentration | Time Offset | MSO Sensor Status Annunciation (if present) |
|---|---|---|---|---|
| Byte Order | LSO ... MSO | LSO ... MSO | LSO ... MSO | LSO ... MSO |
| Data type | UINT8 | SFLOAT | UINT16 | 8, 16 or 24 bit* |
| Size | 1 octet | 2 octets | 2 octets | 0, 1, 2 or 3 octets* |
| Units | None | mg/dL | Minutes | None |

* If Status Extension bit(s) is set to "1" number of octets/bits increases

The size field represents the size of the CGM measurement record. The minimum size of a CGM measurement record is 5 octets. The size increases depending on the value of the sensor status annunciation field. The CGM glucose concentration field contains glucose concentrations measured in mg/dL. The glucose concentrations are stored in a SFLOAT data type which is a 16-bit word that includes a 4-bit integer exponent followed by a signed 12-bit Mantissa, each in twos-complement form. The time offset field specifies the relative time difference between the time at which the CGM value was taken and the session start time. The sensor status annunciation field indicates the status of the CGM 200. The sensor status annunciation field can indicate any one or more of the following statuses:

| Bit | Definition |
|---|---|
| 0 | Time synchronization between sensor and collector required |
| 1 | Calibration not allowed |
| 2 | Calibration recommended |
| 3 | Calibration required |
| 4 | Sensor result lower than the Patient Low level |
| 5 | Sensor result higher than the Patient High level |
| 6 | Sensor result lower than the Hypo level |
| 7 | Sensor result higher than the Hyper level |
| 8 | Sensor Rate of Decrease exceeded |
| 9 | Sensor Rate of Increase exceeded |
| 10 | Device Specific Alert |
| 11 | Sensor malfunction |
| 12 | Sensor temperature too high for valid test/result at time of measurement |

-continued

| Bit | Definition |
|---|---|
| 13 | Sensor temperature too low for valid test/result at time of measurement |
| 14 | Sensor result lower than the device can process |
| 15 | Sensor result higher than the device can process |
| 16 | Session stopped |
| 17 | Device battery low |
| 18 | Sensor type incorrect for device |
| 19 | General device fault has occurred in the sensor |
| 20 | Reserved for Future Use |
| 21 | Reserved for Future Use |
| 22 | Reserved for Future Use |
| 23 | Status Extension |

As an example, if an amount of charge remaining in the power source 429 of the CGM 200 is lower than a particular threshold charge, then bit 17 of the sensor status annunciation field is set to 'True' or '1' to indicate that the device battery is low. Other encoding schemes are also contemplated.

In an alternative embodiment, the status of the CGM 200 is acquired independent of the CGM measurements (i.e. the status of the CGM 200 is recorded even when the blood glucose sensor 421 is not collecting blood glucose concentration levels). In this embodiment, the CGM status is stored in a CGM status field that is similar to the sensor status annunciation field.

The CGM measurement module 602 acquires blood glucose measurements periodically and stores the measurements in the CGM measurement datastore 604. The CGM measurement module 602 acquires new measurements at fixed time intervals, for example every one second, every five seconds, etc. Other time intervals are also contemplated.

The CGM measurement datastore 604 has a maximum capacity and when the CGM measurement datastore 604 reaches its maximum capacity then CGM measurements are selectively deleted or purged. In this embodiment, the oldest CGM measurement is purged. In an alternative embodiment, when there are duplicate consecutive CGM measurements then the older duplicate CGM measurement is purged. In another alternative embodiment, CGM measurements are selectively purged based on a value of their corresponding sensor status annunciation field. For example, the oldest CGM measurement in which all the bits corresponding with the sensor status annunciation field have a value of '0' or 'False' is purged.

The message generation module 610 periodically obtains a CGM measurement from the CGM measurement datastore 604 and generates a message that contains the CGM measurement. In this embodiment, the message generation module 610 obtains a single CGM measurement from the CGM measurement datastore 604. In an alternative embodiment, the message generation module 610 obtains multiple CGM measurements from the CGM measurement datastore 604.

In this embodiment, the message generation module 610 obtains a CGM measurement from the CGM measurement datastore 604 as soon as a new CGM measurement is stored in the CGM measurement datastore 604. In an alternative embodiment, the message generation module 610 obtains the CGM measurement from the CGM measurement datastore 604 at fixed time intervals (e.g. every five seconds, every one minute, every one hour, etc). Other time periods for the message generation module 610 to obtain measurements from the CGM measurement datastore 604 are also contemplated.

The message generation module 610 generates a message that contains the CGM measurement. Alternatively, when the message generation module 610 obtains multiple CGM measurements, the message generation module 610 generates a message that contains all the CGM measurements that were obtained.

The message generation module 610 appends a CGM status to the message. In this embodiment, the CGM status is determined by comparing the CGM measurement with a threshold. For example, if the CGM measurement is lower than a threshold corresponding with a lower end of a patient's blood glucose range, then the status is 'sensor result lower than Patient Low level' to the message. In this embodiment, the message can include a CGM status in addition to a CGM measurement. In an alternative embodiment, the message generation module 610 generates a message that only includes a CGM status and not a CGM measurement. An example of a CGM status is a 'device battery low' status. The CGM status is stored in a sensor status annunciation field.

The message generation module 610 appends any other fields that are necessary to transmit the message to the diabetes manager 104. For example, the message generation module 602 appends a header field to the message.

The message also includes a timestamp. The timestamp represents the time at which the measurement was taken by the CGM measurement module 602 or the time at which the message was generated. In this embodiment, the message is generated as soon as the measurement is taken.

The message generation module 610 stores the generated messages in the message datastore 611. Alternatively, the message generation module 610 stores the generated messages in the message datastore 611 when the CGM 200 is not within the communication range of another medical device, for example the diabetes manager 104.

The elapsed time determination module 612 determines an amount of time that has elapsed since the transceiver 423 of the CGM 200 last transmitted data.

The elapsed time determination module 612 generates a timestamp every time the transceiver 423 transmits data. The elapsed time determination module 612 stores the timestamps in the memory 427 and compares the most recently stored timestamp with a current time. The elapsed time determination module 612 determines the elapsed time by computing a difference between the most recently stored timestamp at which the transceiver 423 last transmitted data and the current time.

In an alternative embodiment, the elapsed time determination module 612 determines the elapsed time by computing a time difference between a current time and a time at which the last acknowledge message (ACK) was received from another medical device, such as the diabetes manager 104.

Sometimes the diabetes manager 104 is out of range which prevents the CGM 200 from successfully transmitting messages to the diabetes manager 104. For example, if the CGM 200 and the diabetes manager 104 are configured to communicate via Bluetooth and the patient 100 places the diabetes manager 104 in a location that is outside the Bluetooth range of the CGM 200 (e.g. more than 100 meters), then the diabetes manager 104 will not receive any messages sent by the CGM 200 during the out-of-range period.

The elapsed time determination module 612 obtains a first time threshold from the time threshold datastore 613 and compares an amount of time that has elapsed since the transceiver 423 last transmitted data with the first time threshold. If the elapsed time is greater than the first time threshold, then the elapsed time determination module 612 notifies the message prioritization module 614. An example value for the first time threshold is five minutes.

The message prioritization module 614 determines priorities of messages stored in the message datastore 611. During the time period in which the CGM 200 is not able to successfully transmit messages to the diabetes manager 104, the messages are stored in the message datastore 611. Depending on the length of time during which there was no successful transmission from the CGM 200 to the diabetes manager 104, there may be several messages stored in the message datastore 611. If the CGM 200 has not successfully transmitted data for a long time period (e.g. 2 days) then there may be tens or even hundreds of messages stored in the message datastore 611. The message prioritization module 614 determines a priority for each message in the message datastore 611, so that when the CGM 200 is able to successfully transmit data to the diabetes manager 104 then the messages with the highest priority are sent before the messages with relatively low priority, regardless of the time at which the messages were generated. Advantageously, by transmitting messages with higher priorities before transmitting messages with relatively lower priorities, the likelihood of the higher priority messages being transmitted and be seen by the user increases thereby leading to better management of the patient's diabetic condition.

In this example embodiment, the message prioritization module 614 prioritizes the messages based on a value of the sensor status annunciation field of the messages.

A sensor status annunciation field value of 'calibration required' is given higher priority than a sensor status annunciation field value of 'calibration recommended'. Consequently, if the message datastore 611 contains a first message in which the sensor status annunciation field indicates that calibration is recommended and a second message in which the sensor status annunciation field indicates that calibration is required, then the second message (calibration required) is given a higher priority than the first message (calibration recommended) even though the second message was generated after the first message was generated.

A sensor status annunciation field value of 'sensor result lower than the Hypo level' is given higher priority than a sensor status annunciation field value of 'sensor result lower than the Patient Low level'. Similarly, a sensor status annunciation field value of 'sensor result higher than the Hyper level' is given higher priority than a sensor status annunciation field value of 'sensor result higher than the "Patient" Hyper level'.

A message indicating that a patient's blood glucose concentration is lower than expected is given higher priority than a message indicating that a patient's blood glucose concentration is higher than expected because critically low blood glucose concentrations are more problematic than high blood glucose concentrations.

In another example embodiment, the message prioritization module 614 prioritizes the messages based on the type of the messages. The following exemplary message types are listed in descending order of priority:

| Priority | Message Type | Example messages |
| --- | --- | --- |
| 1) | Error messages | e.g. Calibration required |
| 2) | Maintenance messages | e.g. Calibration recommended |
| 3) | Warning messages | e.g. Calibration not allowed |
| 4) | Reminder messages | e.g. Device battery low |
| 5) | Information messages | e.g. Session stopped |

In this embodiment, the message prioritization module 614 assigns an error message a higher priority than a maintenance message, so that the error message is transmitted before the maintenance message is transmitted even if the error message was generated after the maintenance message. The message prioritization module 614 assigns a maintenance message a higher priority than a warning message, so that the maintenance message is transmitted before the warning message even if the maintenance message was generated after the warning message. The message prioritization module 614 assigns a higher priority to a warning message than a reminder message, so that the warning message is transmitted before the reminder message even if the warning message is generated after the reminder message. The message prioritization module 614 assigns a reminder message a higher priority than an information message, so that the reminder message is transmitted before the information message even if the reminder message is generated after the information message.

In this embodiment, the message prioritization module 614 assigns a higher priority to a CGM status message than to a CGM measurement message even when the CGM status message is generated after the CGM measurement is generated. Advantageously, the user is notified of the CGM status before seeing the CGM measurement because the CGM status may adversely affect CGM measurements.

The message transmittal module 616 transmits messages to the diabetes manager 104 using the transceiver 423. If the elapsed time since the CGM 200 last transmitted data is less than a first time threshold, then the message transmittal module 616 transmits messages in the order that the message were generated. However, if the elapsed time is greater than the first time threshold, then the message transmittal module 616 sorts the messages based on the priority assigned to the messages by the message prioritization module 614. The message transmittal module 616 transmits a message with a higher priority before transmitting a message with a relatively lower priority even if the message with the higher priority was generated after the message with the lower priority. Advantageously, if the communication link between the CGM 200 and the diabetes manager 104 is weak and intermittent then, by changing the order in which the messages are transmitted from the CGM 200 to the diabetes manager 104, the messages with higher priority are more likely to be transmitted to the diabetes manager 104.

If the elapsed time since the CGM 200 last transmitted data is greater than a second time threshold stored in the time threshold datastore 613, then the message transmittal module 616 inserts all messages from the message datastore 611 that need to be transmitted into a file. The message transmittal module 616 orders the messages so that the higher priority messages are towards the beginning of the file and the lower priority messages are towards the end of the file. The second time threshold is set at a value greater than the first time threshold. For example, if the first time threshold is five minutes, then the second time threshold may be 10 minutes. Advantageously, when the CGM 200 and the diabetes manager 104 have been out of communication for an extended time duration then the user does not get overwhelmed with numerous separate messages, instead the user receives a single file with all the messages in the file which can also be triaged on the diabetes manager 104.

The diabetes manager 104 includes a message receiving module 630 and a message presentation module 650.

The message receiving module 630 receives messages from the CGM 200 via the transceiver 402. The message receiving module 630 receives individual messages or, alternatively, the message receiving module 630 receives a file containing several messages.

The message presentation module 650 presents the messages received by the message receiving module 630 by outputting them via the user interface 406. In an example embodiment, the message presentation module 650 selectively varies the presentation of the messages based on the priority of the message or the type of the message. For example, when the message presentation module 650 presents an error message then the message presentation module 650 displays the message on a display of the diabetes manager 104, emits a sound through a speaker of the diabetes manager 104 and causes the diabetes manager 104 to vibrate by activating a vibration motor of the diabetes manager 104. By contrast, when the message presentation module 650 presents an information message then the message presentation module 650 simply displays the message on the display of the diabetes manager 104 without emitting a sound through the speaker and without causing the diabetes manager 104 to vibrate. Advantageously, by selectively varying the presentation style of the messages, there is an increased likelihood that the higher priority messages will be noticed by the user of the diabetes manager 104.

Figure 7:
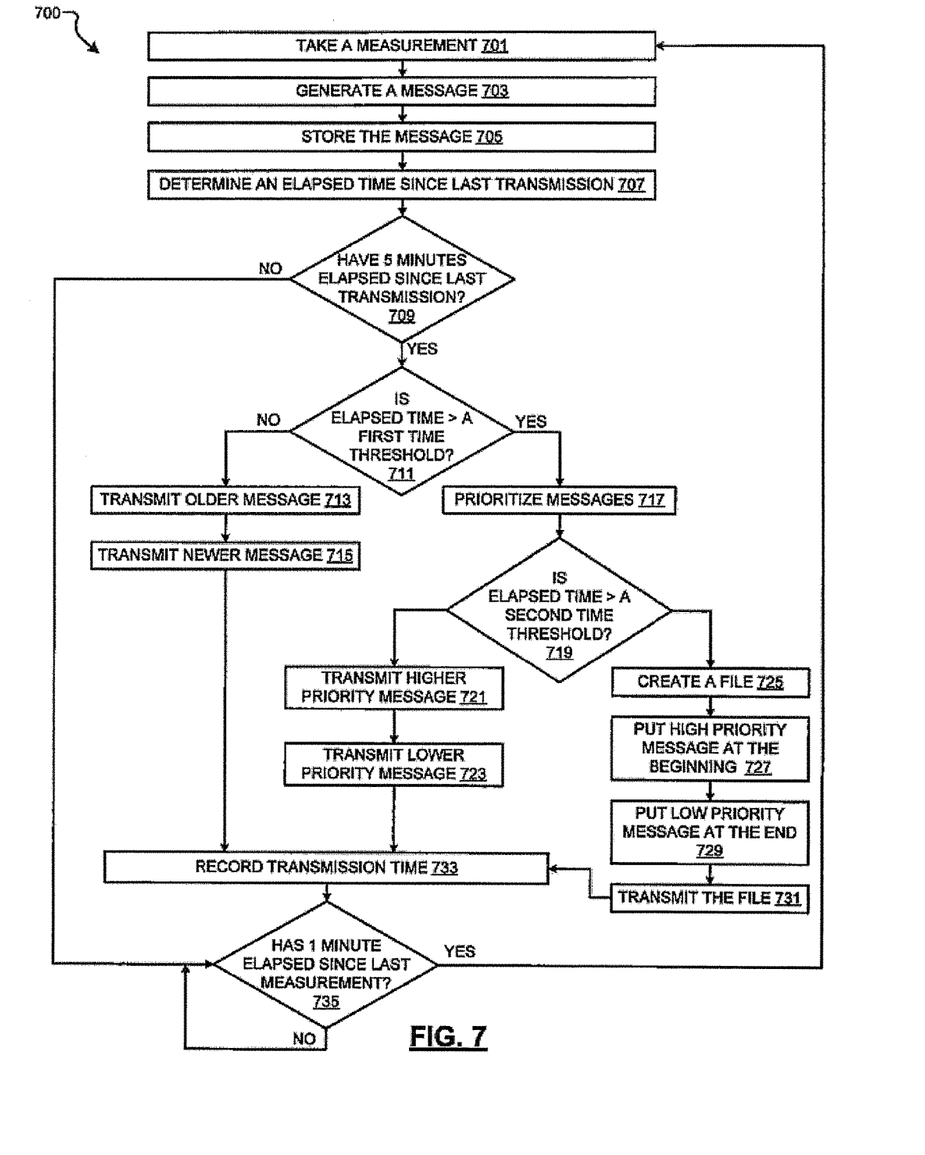
FIG. 7 is a flow diagram illustrating an example method for transmitting messages generated by a CGM.

FIG. 7 is a flow diagram illustrating an example method for transmitting messages generated by the CGM 200.

The CGM measurement module 602 uses the blood glucose sensor 421 of the CGM 200 to take a blood glucose concentration measurement (Step 701). The measurement is stored in the CGM measurement datastore 604.

The message generation module 610 obtains the measurement from the CGM measurement datastore 604 and generates a message (Step 703). The message generation module 610 appends a CGM status to the message and stores the message in the message datastore 611 (Step 705).

The elapsed time determination module 612 determines an amount of time that has elapsed since the CGM 200 last transmitted data (Step 707). If five minutes or more have elapsed since the last transmission, then it is time to transmit messages again (Step 709). In this embodiment, the message transmission frequency is five minutes; however, other frequencies are also contemplated. Advantageously, by transmitting messages less frequently than the rate at which the messages are generated, the CGM 200 consumes less power.

Next, it is determined whether the messages are to be prioritized before the messages are transmitted. This determination is made by comparing the elapsed time with a first time threshold (Step 711). Alternatively, this determination can be made by comparing the number of messages stored in the message datastore 611 with a threshold.

If the elapsed time is less than a first time threshold, then the messages are not prioritized. The message transmittal module 616 transmits the older message first (Step 713) and then transmits the newer message (Step 714).

If, however, the elapsed time is greater than the first time threshold, then the message prioritization module 614 prioritizes the messages (Step 717).

Once the messages have been prioritized, it is determined whether the messages are to be transmitted individually or as part of a file. This determination is made by comparing the elapsed time with a second time threshold (Step 719).

If the elapsed time is less than the second time threshold, then the messages are transmitted individually. The message transmittal module 616 transmits the higher priority message first (Step 721) and then transmits the lower priority message (Step 723).

If, however, the elapsed time is greater than the second time threshold, then the messages are transmitted as part of a file. The message transmittal module 616 creates a file (Step 725), inserts the higher priority message at the beginning of the file (Step 727), the lower priority message at the end of the file (729) and transmits the file (Step 731).

The message transmittal module 616 records the time at which the last message was transmitted (Step 733). This timestamp is stored in the memory 427 and is used by the elapsed time determination module 612 to determine the elapsed time since the last transmission (at Step 707).

If one minute has elapsed since the last measurement, then another measurement is taken (Step 735) and the method repeats. In this embodiment, the measurement frequency is one minute; however, other frequencies are also contemplated.

Figure 8:
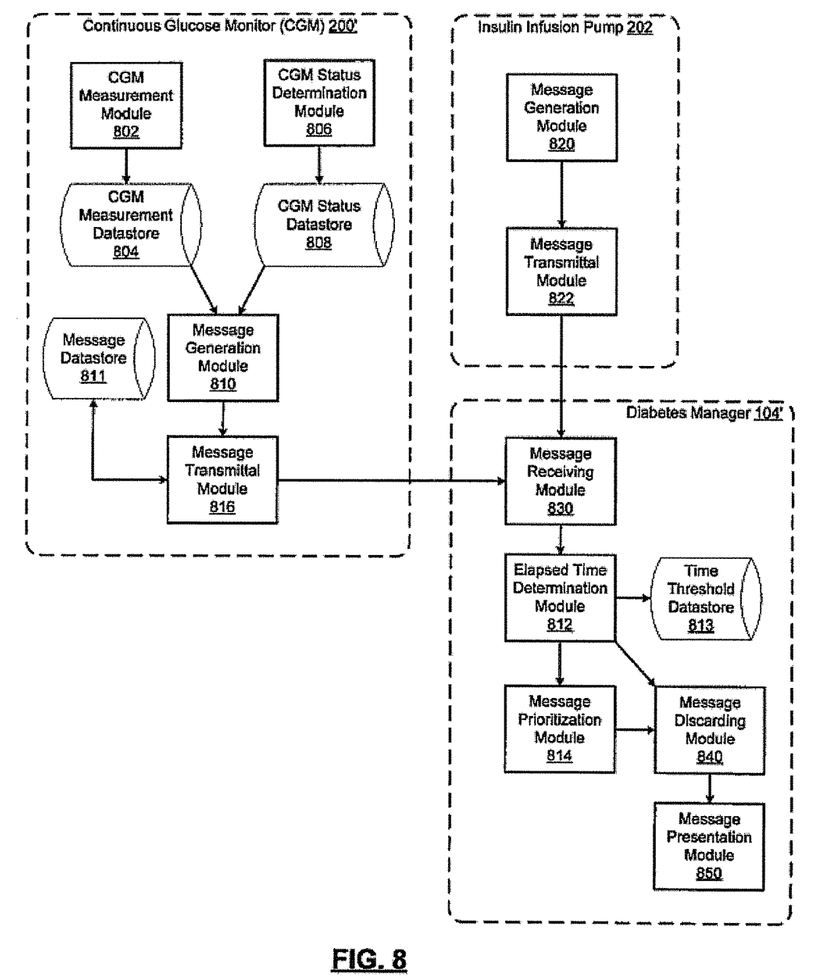
FIG. 8 is a block diagram illustrating another example CGM and another example diabetes manager.

FIG. 8 is a block diagram illustrating an example embodiment in which a CGM 200' and an insulin infusion pump 202 are interfaced with a diabetes manager 104'. The CGM 200' includes a CGM measurement module 802, a CGM measurement datastore 804, a CGM status determination module 806, a CGM status datastore 808, a message generation module 810 and a message transmittal module 816.

The CGM measurement module 802 is similar to the CGM measurement module 602. The CGM measurement module 802 uses the blood glucose sensor 421 to acquire blood glucose concentrations of a patient. The CGM measurement module 802 stores the CGM measurements in the CGM measurement datastore 804.

The CGM status determination module 806 determines the status of the CGM 200'. The CGM status determination module 806 stores the CGM status in the CGM status datastore 808. The CGM status is stored in a CGM status field that is similar in structure to the sensor status annunciation field discussed above.

The message generation module 810 obtains a CGM measurement from the CGM measurement datastore 804 and generates a CGM measurement message which contains the CGM measurement. The message generation module 810 obtains a CGM status from the CGM status datastore and generates a CGM status message which contains the CGM status.

The message transmittal module 816 uses the transceiver 423 to transmit the messages generated by the message generation module 810 to the diabetes manager 104'. In this example embodiment, the message transmittal module 816 transmits the messages as soon as the messages are generated by the message generation module 810. If, however, the message transmittal module 816 is unable to successfully transmit the messages, then the message transmittal module 816 stores the messages in a message datastore 811, so that the message transmittal module 816 can attempt to transmit the messages at a later time.

In this embodiment, the messages generated by the CGM 200' are not prioritized by the CGM 200' before the CGM 200' transmits the messages to the diabetes manager 104'. This is different from the embodiment depicted in FIG. 6 in which the CGM 200 prioritized the messages the CGM 200 generated before the messages were transmitted to the diabetes manager 104.

The insulin infusion pump 202 includes a message generation module 820 and a message transmittal module 822.

The message generation module 820 generates messages regarding the operation and status of the insulin infusion pump 202. An example message generated by the message generation module 820 indicates an amount of insulin that was delivered by the insulin infusion pump 202. Another example message indicates a status of the insulin infusion pump 202. An example status is a low battery status.

The message transmittal module 822 transmits the messages generated by the message generation module 820 through a transmitter of the insulin infusion pump 202. The message transmittal module 822 transmits the messages to the diabetes manager 104'.

The diabetes manager 104' includes a message receiving module 830, and elapsed time determination module 812, a message prioritization module 814, a message discarding module 840 and a message presentation module 850.

The message receiving module 830 receives messages from healthcare devices, such as the CGM 200' and the insulin infusion pump 202, through the transceivers 423.

The elapsed time determination module 812 determines a length of time that has elapsed since the transceiver 423 last received data. The elapsed time determination module 812 determines the elapsed time by computing a time difference between a current time and a stored timestamp that corresponds with a time at which the transceiver 402 last received data. In an alternative embodiment, the elapsed time determination module 812 determines an amount of time that has elapsed since the transceiver 423 last received an acknowledge message ('ACK' message).

In this embodiment, the elapsed time determination module 812 determines a length of time that has elapsed since the transceiver 423 last received data from any healthcare device. The elapsed time determination module 812 compares the elapsed time with a first time threshold stored in the time threshold data store 813. If the elapsed time is greater than the first time threshold then the elapsed time determination module 812 sends a signal to the message prioritization module 814 and the message discarding module 840 indicating that the elapsed time is greater than the first time threshold.

In an alternative embodiment, the elapsed time determination module 812 determines a first elapsed time that has elapsed since the transceiver 423 last received data from the CGM 200' and a second elapsed time that has elapsed the transceiver 423 last received data from insulin infusion pump 202. The elapsed time determination module 812 compares the first elapsed time with a first time threshold stored in the time threshold data store 813, the first time threshold corresponds to the CGM 200'. If the first elapsed time is greater than the first time threshold then the diabetes manager 104' has not received any data from the CGM 200' during a time period at least as long as the first time threshold. The elapsed time determination module 812 compares the second elapsed time with a second time threshold stored in the time threshold to the store 813, the second time threshold corresponds to the insulin pump 202. If the second elapsed time is greater than the second time threshold then the diabetes manager 104' has not received any data from the insulin infusion pump 202 during a time period at least as long as the second time threshold.

The message prioritization module 814 is similar to the message prioritization module 614. The message prioritization module 814 prioritizes the messages received by the message receiving module 830. In this embodiment, the message prioritization module 814 only prioritizes the messages when the elapsed time is greater than the first time threshold.

The message prioritization module 814 prioritizes the messages based on a priority associated with each message. If the messages do not have priorities, then the message prioritization module 814 determines priorities for each message based on the type of the message. Example types include an error message, a maintenance message, a warning message, a reminder message and an information message. Alternatively, the message prioritization module 814 prioritizes the messages based on a source of the messages. For example, a message from the insulin infusion pump 202 is assigned a higher priority than a message from the CGM 200'.

The message discarding module 840 discards a first message that is obsolete or no longer relevant in view of a second message that is to be presented via the message presentation module 850. The message discarding module 840 discards a first message based on a first priority associated with the first message and a second priority associated with a second message. In this embodiment, the message discarding module 840 discards a first message when a second message that is generated after the first message has a higher priority than the first message. Alternatively, the message discarding module 840 discards the first message when a second message that is received after the first message makes the first message obsolete or irrelevant.

In an alternative embodiment, the message discarding module 840 discards a first message based on a comparison between a value of a sensor status annunciation field of the first message and a value of a sensor status annunciation field of a second message that is received after the first message. For example, a first message that has a sensor status annunciation field value of 'calibration recommended' is obsolete when a second message that is received after the first message has a sensor status annunciation field value of 'calibration required'. As a result, in this example, the message discarding module 840 discards the first message (calibration recommended) and instructs the message presentation module 850 to present the second message (calibration required).

In another alternative embodiment, the message discarding module 840 discards a first message based on a comparison between a source of the first message and a source of the second message. The message discarding module 840 discards a first message when the first message is received from the CGM 200' and the second message is received from the insulin infusion pump 202.

If the number of messages is greater than a message presentation threshold (e.g. 5, 10, 25, etc) then the message discarding module 840 discards the lowest priority messages in order to reduce the number of messages to a number equal to the message presentation threshold.

The message presentation module 850 is similar to the message presentation module 650. The message presentation module 850 presents the messages that the message discarding module 840 does not discard. The message presentation module 850 selectively varies the presentation of the messages based on the source of the messages. For example, the presentation of a message from the insulin infusion pump 202 includes displaying corresponding data on a display of the diabetes manager 104', emitting a sound through a speaker of the diabetes manager 104' and activating a vibration motor to force the diabetes manager 104' to vibrate. By contrast, a message from the CGM 200' is presented by simply displaying data on the display of the diabetes manager 104'.

Figure 9:
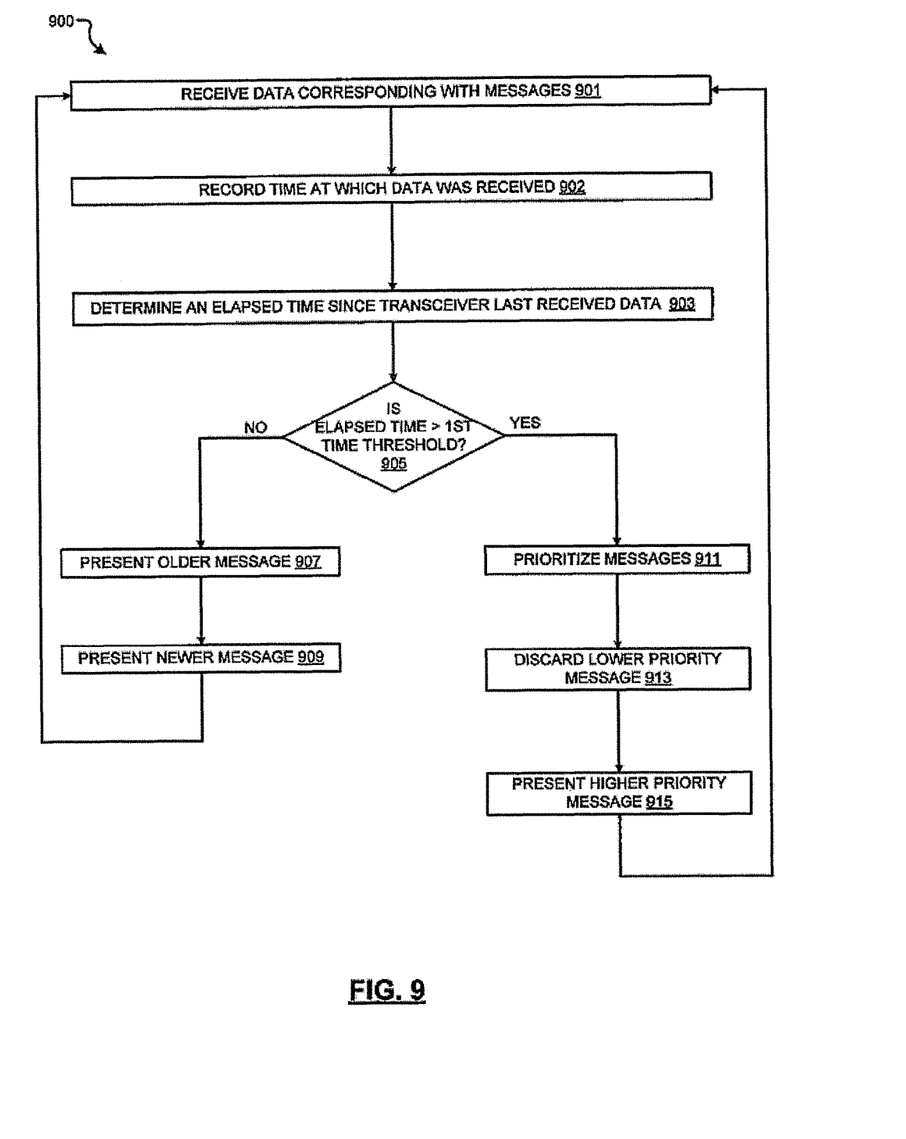
FIG. 9 is a flow diagram illustrating an example method for presenting messages received by the diabetes manager.

FIG. 9 is a flow diagram illustrating an example method 900 for discarding messages received by the diabetes manager 104'.

The message receiving module 830 receives data corresponding with messages from healthcare devices, such as the CGM 200' and the insulin infusion pump 202 (Step 901).

The message receiving module 830 records the time at which the data was received (Step 902) by generating a timestamp and storing the timestamp in the memory 410.

The elapsed time determination module 812 determines an amount of time that has elapsed since the diabetes manager 104' last received data (Step 903). The elapsed time is compared with a first time threshold (at Step 905) in order to determine whether the messages are to be prioritized.

If the elapsed time is less than the first time threshold, then the messages are not prioritized. Instead, the message presentation module 850 presents the older message (Step 907) and then presents the newer message (Step 909).

If, however, the elapsed time is greater than the first time threshold, then the message prioritization module 814 prioritizes the messages (Step 911). After the messages have been prioritized, the message discarding module 840 discards the lower priority message (Step 913) and the message presentation module 850 presents the higher priority message (Step 915).

In this application, including the definitions below, the term module may be replaced with the term circuit. The term module may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor (shared, dedicated, or group) that executes code; memory (shared, dedicated, or group) that stores code executed by a processor; other suitable hardware components that provide the described functionality; or a combination of some or all of the above, such as in a system-on-chip.

The term code, as used above, may include software, firmware, and/or microcode, and may refer to programs, routines, functions, classes, and/or objects. The term shared processor encompasses a single processor that executes some or all code from multiple modules. The term group processor encompasses a processor that, in combination with additional processors, executes some or all code from one or more modules. The term shared memory encompasses a single memory that stores some or all code from multiple modules. The term group memory encompasses a memory that, in combination with additional memories, stores some or all code from one or more modules. The term memory may be a subset of the term computer-readable medium. The term computer-readable medium does not encompass transitory electrical and electromagnetic signals propagating through a medium, and may therefore be considered tangible and non-transitory. Non-limiting examples of a non-transitory tangible computer readable medium include nonvolatile memory, volatile memory, magnetic storage, and optical storage.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A computer implemented method for transmitting messages generated by a continuous glucose monitor (CGM), the method comprising:

generating a first message at the CGM at a first time, the first message including a glucose measurement;

generating a second message at the CGM at a second time, the second time being after the first time, the second message including a glucose measurement;

determining, by a processor of the CGM, an elapsed time since a transmitter of the CGM has transmitted data;

determining, by the processor, whether the elapsed time is greater than a first threshold;

in response to a determination that the elapsed time is less than the first threshold, transmitting, via a transmitter of the CGM, the first message over a wireless communication link to a diabetes management device, the first message being transmitted prior to the second message and;

in response to a determination that the elapsed time exceeds the first threshold, prioritizing, by the processor, the first message and the second message using a priority assigned to and encapsulated in each of the first message and the second message; and in response to a determination that the elapsed time exceeds the first threshold, transmitting, via the transmitter, the second message over the wireless communication link to the diabetes management device, the second message being transmitted prior to the first message in accordance with the priority assigned to the second message.

2. The computer implemented method of claim 1, wherein the determining whether the second message is to be transmitted before the first message is based on the priority of the second message.

3. The computer implemented method of claim 1, further comprising storing data corresponding with the second message in a memory of the CGM and purging data corresponding with the first message from the memory of the CGM, in response to the second message having a higher priority than the first message.

4. The computer implemented method of claim 1, wherein the determining whether the second message is to be transmitted before the first message is based on a value of the second message.

5. The computer implemented method of claim 1, wherein the second message is to be transmitted before the first message when the second message is an error message and the first message is a warning message.

6. A computer implemented method for presenting messages at a diabetes management device, the method comprising:

generating a first message at a first time by a continuous glucose monitor (CGM), the first message includes a glucose measurement;

generating a second message at a second time by the CGM, the second time being after the first time, the second message includes a glucose measurement;

sending the first message from the CGM via a wireless communication link to the diabetes management device;

sending the second message from the CGM via the wireless communication link to the diabetes management device;

determining, by a processor of the diabetes management device, an elapsed time since the diabetes management device has received data from the CGM;

determining, by the processor, whether the elapsed time is greater than a first threshold;

in response to a determination that the elapsed time exceeds the first threshold, prioritizing, by the processor, the first message and the second message using a priority assigned to and encapsulated in each of the first message and the second message;

in response to second message having a higher priority than the first message, presenting the second message before presenting the first message through an output interface of the diabetes management device.

7. A computer implemented method for presenting messages at a diabetes management device, the method comprising:

receiving data corresponding with a first message via a receiver of the diabetes management device, the first message having a first priority associated therewith, the first message including a glucose measurement;

receiving data corresponding with a second message via the receiver, the second message having a second priority higher than the first priority, the second message being received after the first message and including a glucose measurement;

determining, by a processor of the diabetes management device, an elapsed time since the receiver has received data;

determining, by the processor, whether the elapsed time is greater than a first threshold;

in response to a determination that the elapsed time is less than the first threshold, presenting, by the processor, the first message via an output interface of the diabetes management device;

in response to a determination that the elapsed time exceeds the first threshold, prioritizing, by the processor, the first message and the second message using the priority assigned to and encapsulated in each of the first message and the second message;

discarding the first message in response to a determination that the elapsed time exceeds the first threshold; and presenting the second message via an output interface of the diabetes management device in response to a determination that the elapsed time exceeds the first threshold.

8. The computer implemented method of claim 7, wherein the first priority is based on a value of the first message.

9. The computer implemented method of claim 7, wherein the first message is received from a first healthcare device and the second message is received from a second healthcare device; and wherein second message has a higher priority than the first message.

10. The computer implemented method of claim 9, wherein the first healthcare device includes a continuous glucose monitor and the second healthcare device includes an insulin pump.

11. The computer implemented method of claim 7, wherein the first priority is based on a source of the first message.

12. The computer implemented method of claim 7, wherein the first message is to be discarded when the second priority is higher than the first priority.

13. The computer implemented method of claim 7, wherein the first priority is based on a type of the first message.

14. The computer implemented method of claim 7, wherein the first message is a warning message and the second message is an error message; and wherein the second message has a higher priority than the first message.

* * * * *